(12) United States Patent
Lee (10) Patent No.: US 10,744,271 B2
(45) Date of Patent: Aug. 18, 2020

(54) MEDICINE DELIVERY DEVICE

(71) Applicant: DUO-KANG CO., LTD., Taoyuan (TW)

(72) Inventor: Yung-Fu Lee, Taoyuan (TW)

(73) Assignee: DUO-KANG CO., LTD., Taoyuan (TW)

( * ) Notice: Subject to any disclaimer, the term of this patent is extended or adjusted under 35 U.S.C. 154(b) by 249 days.

(21) Appl. No.: 16/034,108

(22) Filed: Jul. 12, 2018

(65) Prior Publication Data

US 2019/0030254 A1 Jan. 31, 2019

(30) Foreign Application Priority Data

Jul. 31, 2017 (TW) .............................. 106125662 A
Jul. 31, 2017 (TW) .............................. 106211212 U (51) Int. Cl.
*A61M 37/00* (2006.01)
*A61M 5/315* (2006.01)
*A61M 5/20* (2006.01)
*A61M 5/32* (2006.01)

(52) U.S. Cl.
CPC ............ *A61M 5/3158* (2013.01); *A61M 5/20* (2013.01); *A61M 5/31513* (2013.01); *A61M 5/31546* (2013.01); *A61M 5/3202* (2013.01); *A61M 2005/2026* (2013.01); *A61M 2005/3152* (2013.01); *A61M 2005/31588* (2013.01); *A61M 2205/581* (2013.01); *A61M 2205/8206* (2013.01)

(58) Field of Classification Search
CPC .......... A61M 5/20; A61M 2005/31588; A61M 2205/581; A61M 2205/8206; A61M 5/31513; A61M 5/31546; A61M 5/3158; A61M 2005/2026; A61M 2205/19; A61M 2205/33; A61M 5/31
See application file for complete search history.

(56) References Cited

U.S. PATENT DOCUMENTS

| | | | |
|---|---|---|---|
| 2005/0171476 A1* | 8/2005 | Judson | A61M 5/20 604/131 |
| 2012/0302947 A1* | 11/2012 | Canton | A61M 5/30 604/68 |
| 2014/0221925 A1* | 8/2014 | Kondoh | A61M 5/31568 604/111 |
| 2015/0202367 A1* | 7/2015 | Plaschkes | A61M 5/1452 604/506 |
| 2016/0263324 A1* | 9/2016 | Shaanan | A61M 5/16831 |
| 2016/0296700 A1* | 10/2016 | Kikuchi | A61M 5/3205 |

(Continued)

*Primary Examiner* — Rebecca E Eisenberg
(74) *Attorney, Agent, or Firm* — Guice Patents PLLC (57) ABSTRACT

A medicine delivery device includes a main housing having a guide rail in a bottom side thereof, a main control unit with built-in control program mounted in the main housing, a transmission module mounted in the main housing and electrically coupled to the main control unit, the transmission module including a transmission unit, transmission shaft rotatable by the transmission unit and a push rod threaded into the transmission shaft with an axial guide groove thereof coupled to the guide rail for axial displacement upon rotation of the transmission shaft, a push-button unit mounted on the outer surface of the main housing and electrically coupled to the main control unit, and a power supply unit mounted in the main housing for providing the main control unit with the necessary working electricity.

20 Claims, 6 Drawing Sheets

(56) References Cited

U.S. PATENT DOCUMENTS

2017/0151388 A1* 6/2017 Monrad ................ A61M 5/20
2018/0193564 A1* 7/2018 Dahmani ............... A61M 5/46
2018/0311438 A1* 11/2018 Stamp .................. A61M 5/20
2020/0121769 A1* 4/2020 Chang .................. A61K 33/06

* cited by examiner

MEDICINE DELIVERY DEVICE

BACKGROUND OF THE INVENTION

1. Field of the Invention

The present invention relates to syringe technology and more particularly, to a medicine delivery device with automatic control.

2. Description of the Related Art

In the current common medical practice, conventional drugs are prescribed by injecting drugs, and the injecting drugs are carried out by the medical staff or the patient by using a syringe. For example, a diabetic patient is injected with a predetermined insulin dose by himself without needing to go back to the clinic or hospital for injection by a medical staff.

In order to facilitate the use of injection devices for drugs other than medical personnel, there are many injection devices designed for this purpose, such as pre-filled disposable injection devices and reusable pen injection devices. These pre-filled disposable injection devices are relatively simple in design, like the conventional syringes. The difference is that pre-filled disposable injection devices are usually made by pharmaceutical companies or aseptic filling package providers. For the advantage that the users do not need to fill drugs, the use of pre-filled disposable injection devices is quite convenient, however because pre-filled disposable injection devices are not reusable, they are not environmentally friendly and must be professionally recycled to avoid pollution.

Reusable pen injection devices eliminate the drawbacks of pre-filled disposable injection devices and can be refilled for repeated use. These pen-type injection devices are designed to be injected through an automatic mechanism. The automatic mechanism compresses the drug for injection. The automatic mechanism can push the needle into the skin for injection, and can also bring back the needle after injection, avoiding injuring others. Although the automatic mechanism of such a pen-type injection device is convenient in use, the assembly of the automatic mechanism is complicated and and the component parts thereof are diverse, and the mechanism is prone to structural failure. These pen-type injection devices still have disadvantages.

Either the aforesaid pre-filled disposable injection devices or reusable pen injection devices Regardless of the aforementioned pre-filled disposable injection devices or reusable pen injection devices, there is common drawback, that is, pre-filled disposable injection devices and reusable pen injection devices must be manipulated by a person. Different users may exert different forces. Further, there are different injection characteristics for different drugs. There may be deviations in efficiency that require further improvement.

SUMMARY OF THE INVENTION

The present invention has been accomplished under the circumstances in view. It is main object of the present invention to provide a medicine delivery device, which is provided with a transmission module in the device and cooperates with electronic control to match the injection of different drugs, and, which is controlled by a program to drive the transmission module in providing different injection power, improving the injection efficiency of drugs.

To achieve this and other objects of the present invention, a medicine delivery device comprises a main housing, which comprises an accommodation chamber and at least one guide rail in a bottom side of the accommodation chamber, a main control unit accommodated in the main housing and having a control program built therein for controlling the functional operation of the medicine delivery device, and a transmission module accommodated in the accommodation chamber of the main housing and electrically coupled to the main control unit. The transmission module comprises a transmission unit that is the power source of the transmission module, a transmission shaft that is a hollow shaft coupled to and rotatable by the transmission unit, a push rod threaded into the transmission shaft and having at least one axial guide groove located on the periphery thereof and coupled to the at least one guide rail such that the push rod is forced to move axially upon rotation of the transmission shaft, a push-button unit mounted at an outer surface of the main housing and electrically coupled to the main control unit, a trigger unit mounted on the main housing and electrically coupled to the main control unit and the transmission module for driving the transmission module to work, and a power supply unit mounted in the main housing and electrically coupled to the main control unit for providing electricity to the main control unit.

Other advantages and features of the present invention will be fully understood by reference to the following specification in conjunction with the accompanying drawings, in which like reference signs denote like components of structure.

DETAILED DESCRIPTION OF THE PREFERRED EMBODIMENT

Figure 1:
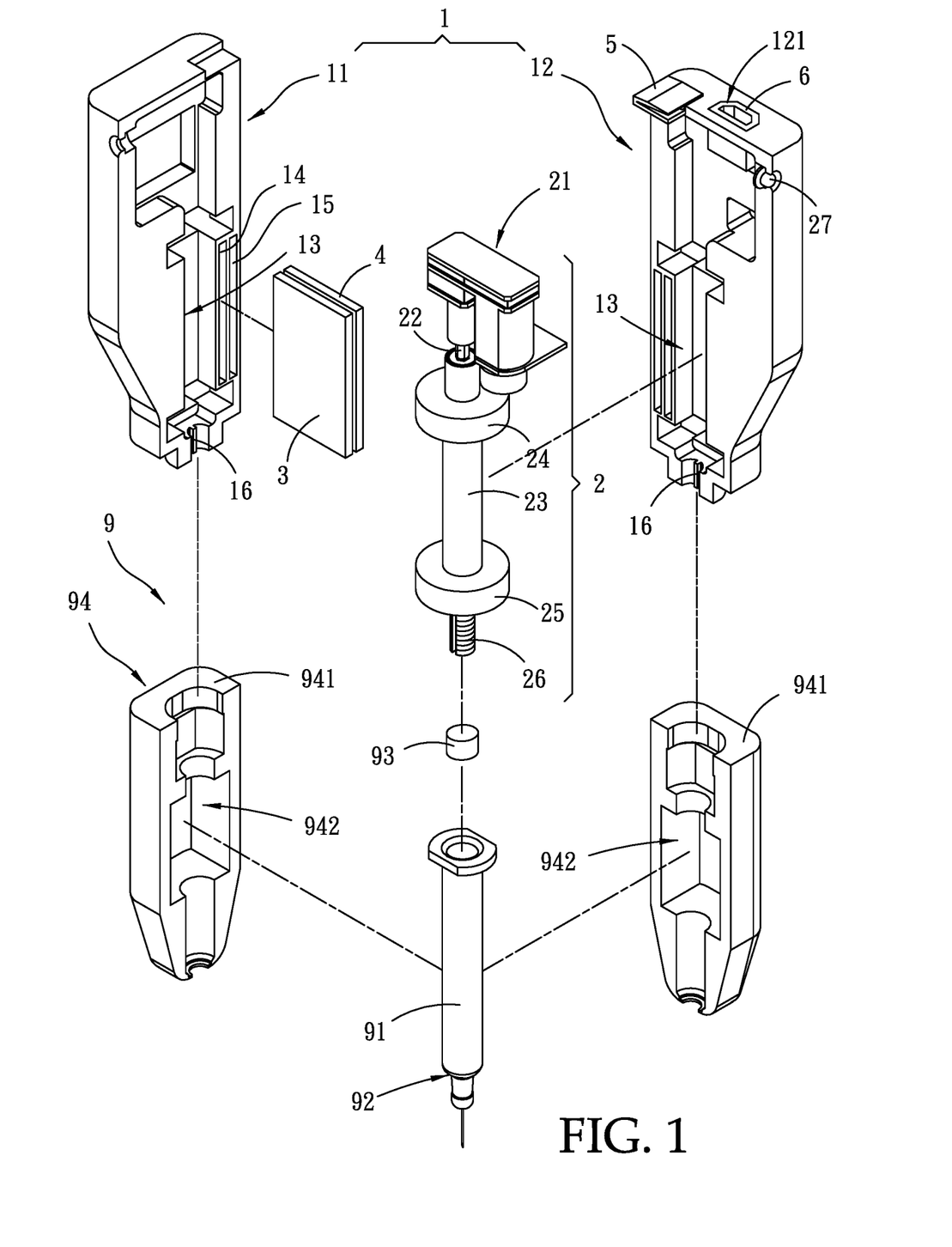
FIG. 1 is an exploded view of a medicine delivery device in accordance with the present invention.

Referring to FIG. 1, a medicine delivery device in accordance with the present invention is shown. The medicine delivery device comprises a main housing 1 and a transmission module 2.

The main housing 1 consists of a first shell 11 and a second shell 12. In this embodiment, the first shell 11 and the second shell 12 are connected to each other. The transmission module 2 is accommodated in the main housing 1. The first shell 11 and the second shell 12 are connected to each other, defining therein an accommodation chamber 13 that accommodates the component parts of the transmission module 2. The main housing 1 comprises a first recessed groove 14 and a second recessed groove 15 defined in each of the first shell 11 and the second shell 12, The first recessed groove 14 is adapted for accommodating a main control unit 3. In this embodiment, the main control unit 3 is a main control circuit board, having built therein a control program for controlling the functional operation of the medicine delivery device 控. The second recessed groove 15 is adapted for accommodating a power supply unit 4. The power supply unit 4 is electrically connected to the main control unit 3 to provide electricity to the main control unit 3 and other component parts that need electricity. In this embodiment, the power supply unit 4 is a rechargeable battery.

Figure 2:
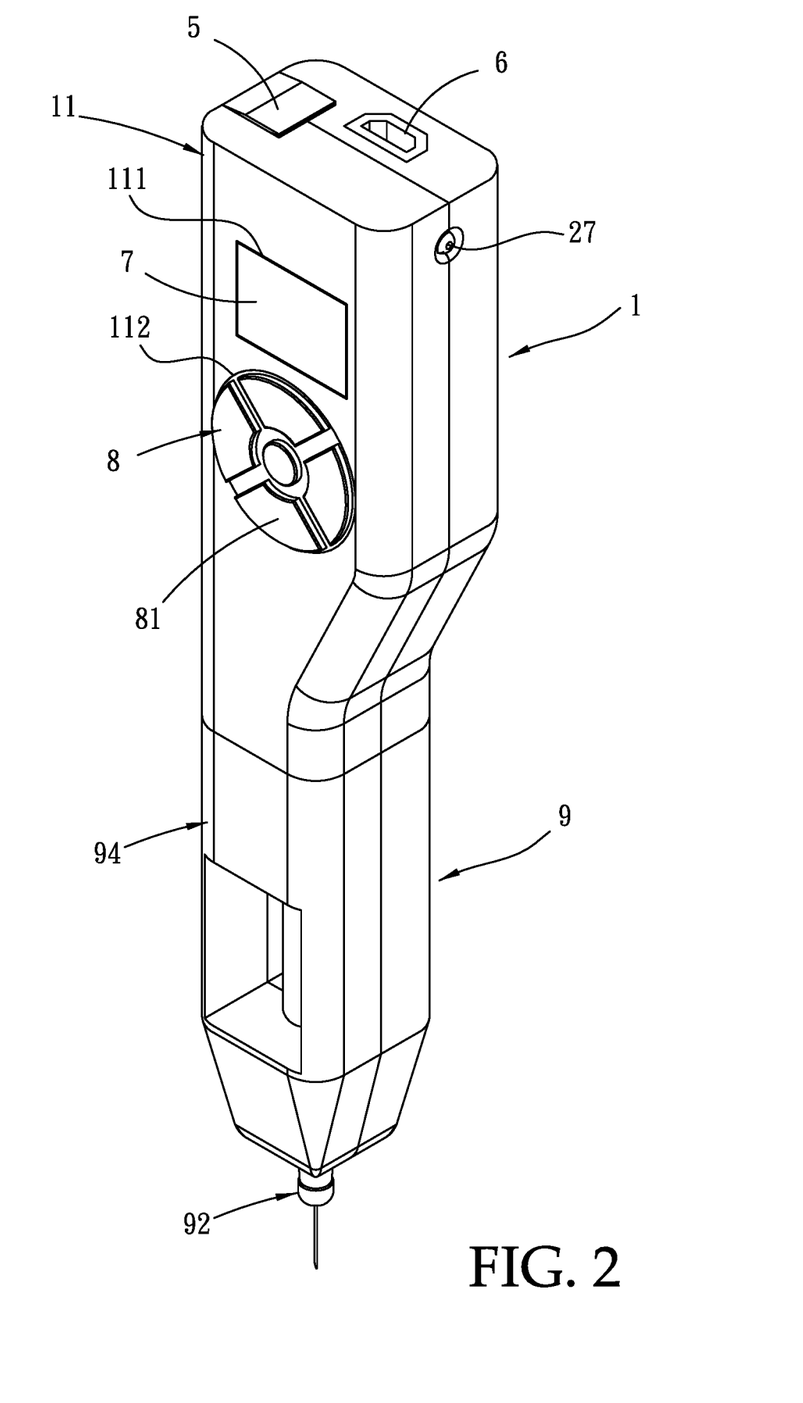
FIG. 2 is an oblique top elevational assembly view of the medicine delivery device in accordance with the present invention.

Referring to FIG. 1 again, a trigger unit 5 is mounted at a top side of the main housing 1 and electrically coupled to the transmission module 2 and the main control unit 3. In this embodiment, the trigger unit 5 is a fire switch for driving the transmission module 2 to work. Further, a connection unit 6 is provided at the top side of the main housing 1. In this embodiment, the second shell 12 comprises a plug hole 121 at a top side thereof for the mounting of the connection unit 6. The connection unit 6 is electrically coupled to the main control unit 3. The connection unit 6 can be, for example, but not limited to, a Micro USB. Through the connection unit 6, the main control unit 3 is electrically connectable to an external host that is operable to update the edition of the built-in program of the main control unit 3. Further, the first shell 11 comprises a mounting groove 111 on the outer surface thereof. In this embodiment, the mounting groove 111 is a rectangular groove for the mounting of a display unit 7, as illustrated in FIG. 2. In this embodiment, the display unit 7 is a micro screen electrically coupled to the main control unit 3 and used to display operating procedures or operating conditions. The first shell 11 further comprises a recessed groove 112 disposed below the display unit 7 for the mounting of a push-button unit 8. The push-button unit 8 is electrically coupled to the main control unit 3. Thee push-button unit 8 consists of a plurality of push-buttons 81. In this embodiment, the recessed groove 112 and the push-button unit 8 exhibit a circular configuration.

Figure 3:
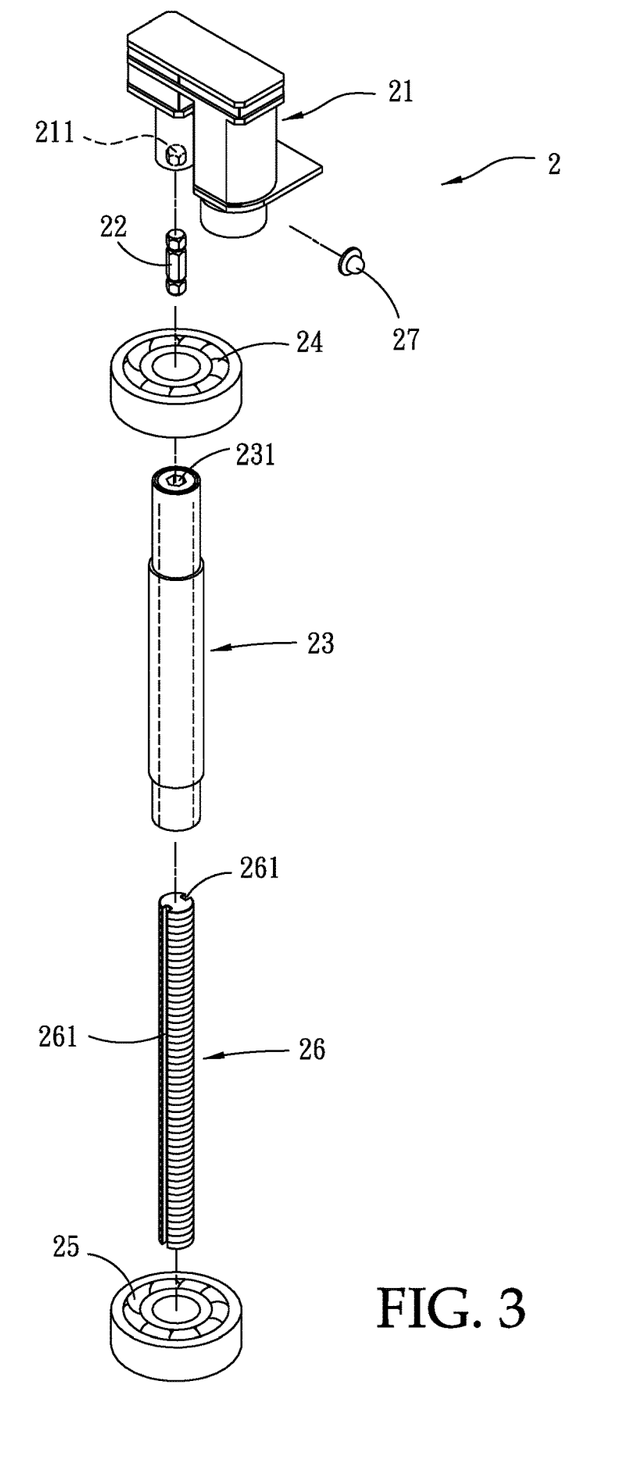
FIG. 3 is an exploded view of the transmission module.
Figure 4:
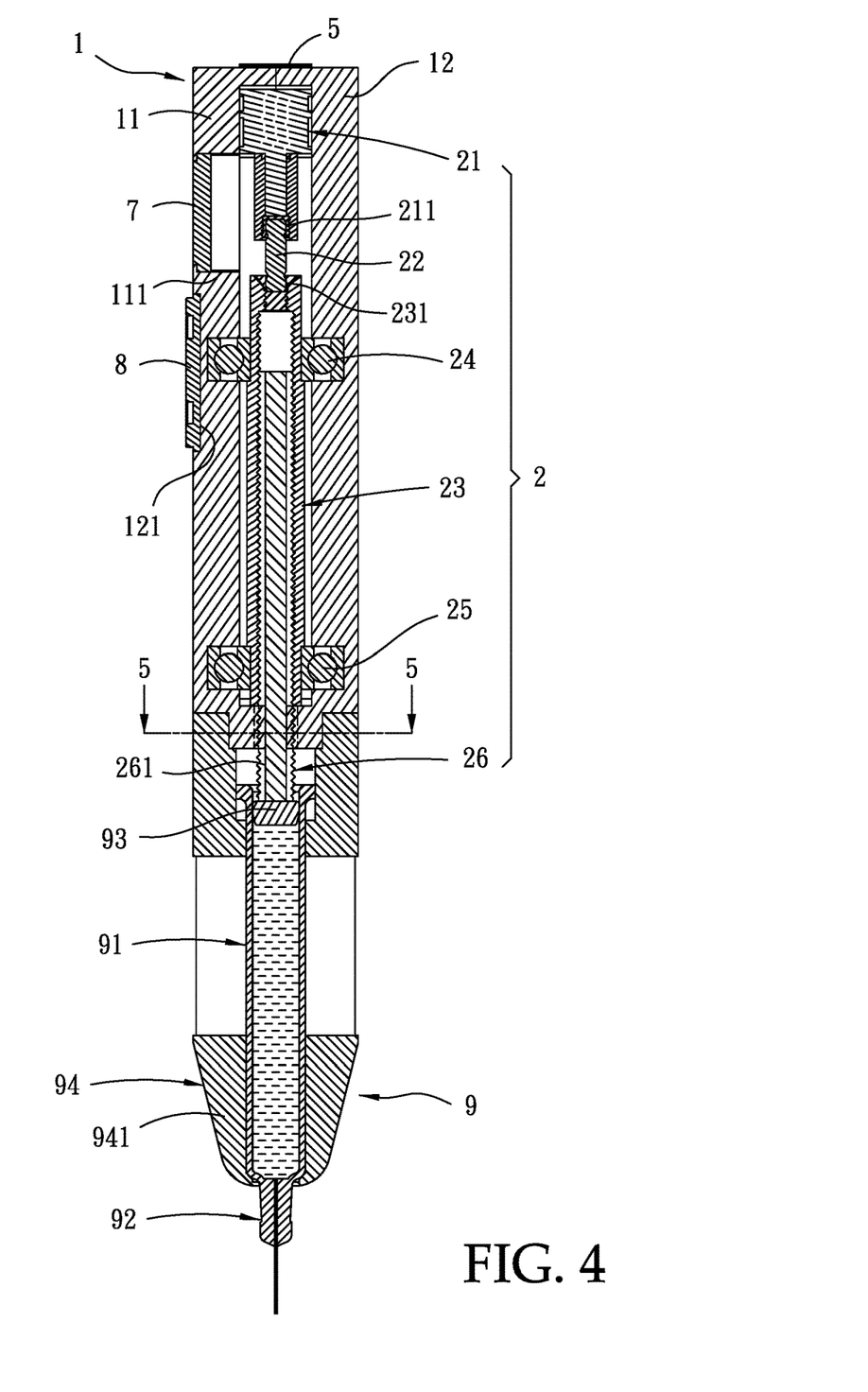
FIG. 4 is a schematic sectional view illustrating an operation status of the present invention.

FIG. 3 is an exploded view of the transmission module. As illustrated, the transmission module 2 is accommodated in the main housing 1 and electrically coupled to the main control unit 3 and the power supply unit 4, as a power source of the medicine delivery device of the present invention. The transmission module 2 comprises a transmission unit 21. The transmission unit 21 is the power source of the transmission module 2. In the embodiment, the transmission unit 21 is any one of a gearbox or a transmission but is not limited thereto. The transmission unit 21 comprises an axle hole 211. The transmission module 2 further comprises an axle 22 that is coupled with one end thereof to the axle hole 211, a transmission shaft 23 that is an internally threaded hollow shaft having a coupling hole 231 located on a top end thereof and coupled to an opposite end of the axle 22 for allowing the transmission shaft 23 to be rotated by the transmission unit 21, a first locating block 24 and a second locating block 25 that are bearings respectively mounted on opposing top and bottom ends of the transmission shaft 23 to support the transmission shaft 23 in the main housing 1 for allowing the transmission shaft 23 to be rotated in the first locating block 24 and the second locating block 25 by the transmission unit 21, a push rod 26 that is a screw rod threaded into the transmission shaft 23, as shown in FIG. 4. The push rod 26 comprises at least one, for example, a plurality of axial guide grooves 261 spaced around the periphery thereof and coupled to respective guide rails 16 in the bottom side of the accommodation chamber 13, as illustrated in FIG. 1. Further, a buzzer 27 is disposed at one lateral side relative to the transmission unit 21. The buzzer 27 is exposed outside the main housing 1 and electrically coupled to the main control unit 3 for making a state sound.

Referring to FIG. 1 again, the medicine delivery device further comprises a syringe module 9 mounted in the bottom side of the main housing 1 in such a manner that the push rod 26 of the transmission module 2 extends to the inside of the syringe module 9. The syringe module 9 comprises a syringe barrel 91 holding therein a liquid medicine, a needle 92 connected to a bottom end of the syringe barrel 91, a movable seal 93 that is a piston slidably mounted in the syringe barrel 91 and drivable by the push rod 26 to expel the liquid medicine out of the syringe barrel 91 through the needle 92, and a protective shell 94 surrounding the syringe barrel 91. In this embodiment, the protective shell 94 consists of two symmetrical shell halves 941, defining therein a shell chamber 942 for accommodating the syringe barrel 91, enabling the needle 92 to be exposed outside the protective shell 94.

Figure 5:
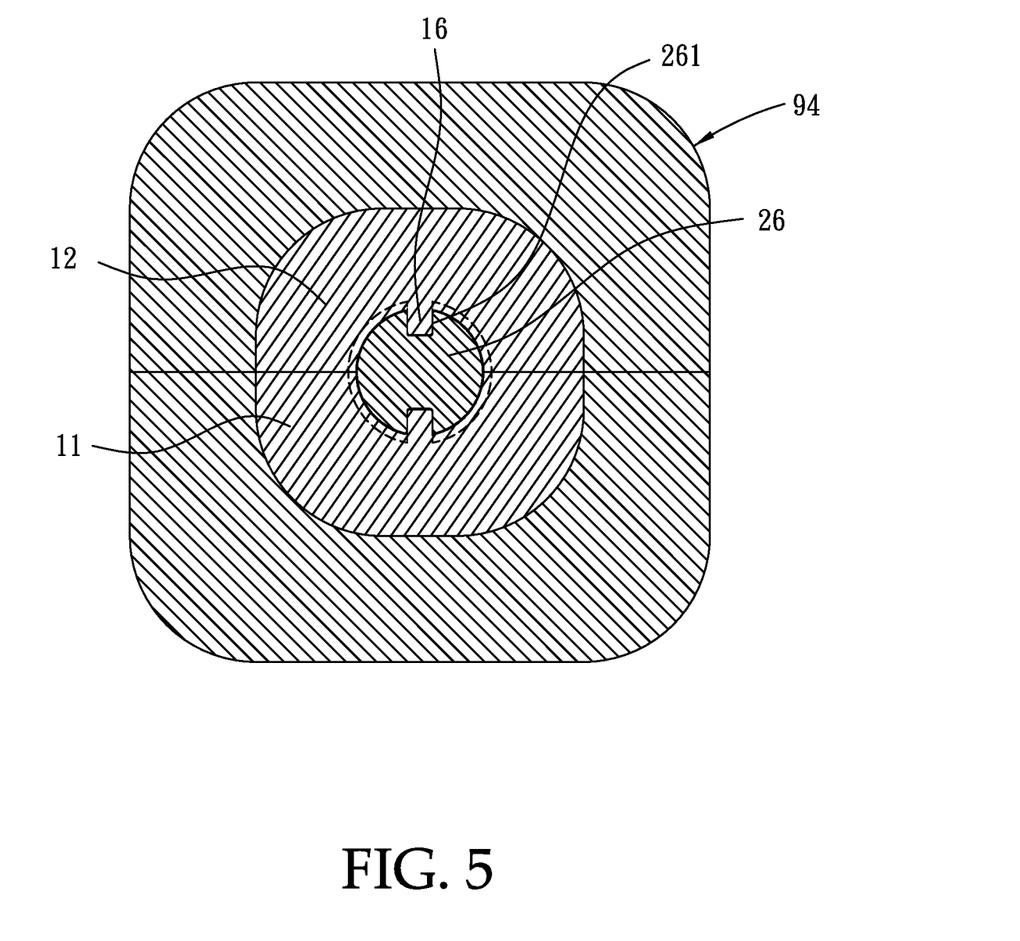
FIG. 5 is a cross sectional structural view of a part of the present invention.
Figure 6:
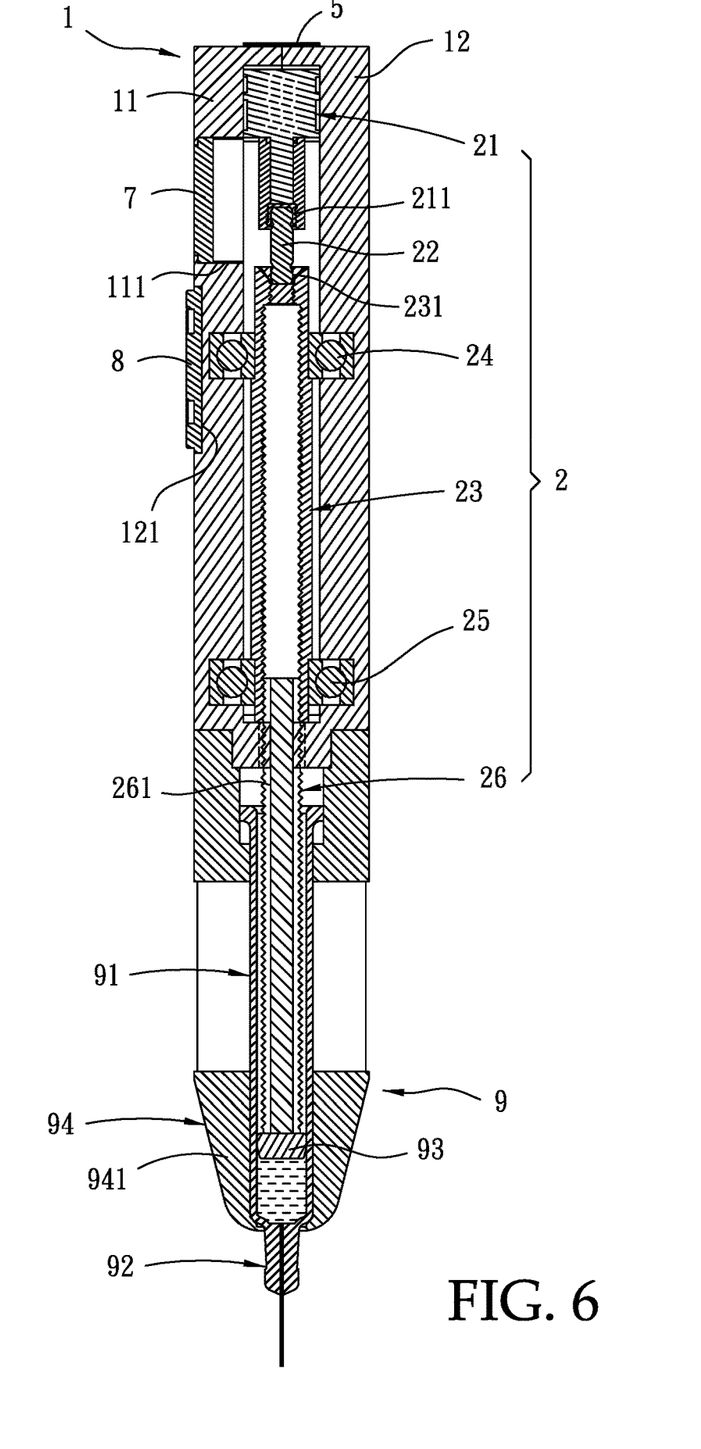
FIG. 6 is a schematic sectional view illustrating another operation status of the present invention.

FIG. 4 is a schematic sectional view illustrating an operation status of the present invention. As illustrated, the medicine delivery device of the present invention configures the delivery speed of different drugs by the program built in the main control unit 3, and the user inputs the type of the syringe module 9 through the push-button unit 8 to control the transmission speed of the transmission module 2. During the operation of the transmission module 2, the transmission unit 21 drives the axle 22 to rotate the transmission shaft 23 horizontally. Subject to the constraint of the coupling arrangement between the axial guide grooves 261 and the respective guide rails 16, as illustrated in FIG. 5, the push rod 26 moves linearly into the inside of the syringe barrel 91 to push the movable seal 93 in the syringe barrel 91 upon rotation of the transmission shaft 23, causing the movable seal 93 to force the internal liquid medicine out of the syringe barrel 91, as illustrated in FIG. 6, achieving precise infusion in an automatic manner.

Although a particular embodiment of the invention has been described in detail for purposes of illustration, various modifications and enhancements may be made without departing from the spirit and scope of the invention. Accordingly, the invention is not to be limited except as by the appended claims.

What the invention claimed is:

1. A medicine delivery device, comprising:
    a main housing comprising an accommodation chamber and at least one guide rail in a bottom side of said accommodation chamber;
    a main control unit accommodated in said main housing and having a control program built therein for controlling the functional operation of the medicine delivery device; and
    a transmission module accommodated in said accommodation chamber of said main housing and electrically coupled to said main control unit, said transmission module comprising:
        a transmission unit being the power source of said transmission module;
        a transmission shaft being a hollow shaft coupled to and rotatable by said transmission unit;
        a push rod threaded into said transmission shaft, said push rod comprising at least one axial guide groove located on the periphery thereof and coupled to said at least one guide rail such that said push rod is forced to move axially upon rotation of said transmission shaft;
        a push-button unit mounted at an outer surface of said main housing and electrically coupled to said main control unit;

a trigger unit mounted on said main housing and electrically coupled to said main control unit and said transmission module for driving said transmission module to work; and a power supply unit mounted in said main housing and electrically coupled to said main control unit for providing electricity to said main control unit.

2. The medicine delivery device as claimed in claim 1, wherein said main housing consists of a first shell and a second shell that are connected to each other.

3. The medicine delivery device as claimed in claim 2, wherein said main housing comprises therein a first recessed groove for accommodating said main control unit and a second recessed groove for accommodating said power supply unit.

4. The medicine delivery device as claimed in claim 3, wherein said main housing consists of a first shell and a second shell, said first shell and said second shell being connected to each other to form therein said first recessed groove and said second recessed groove.

5. The medicine delivery device as claimed in claim 1, wherein said main control unit is a control circuit board.

6. The medicine delivery device as claimed in claim 1, wherein said transmission unit is selectively a gearbox or a transmission.

7. The medicine delivery device as claimed in claim 1, wherein said transmission unit comprises an axle hole, and an axle having one end thereof pivotally coupled to said axle hole; said transmission shaft comprises a coupling hole located on a top end thereof and coupled to an opposite end of said axle for allowing said transmission shaft to be rotated by said transmission unit.

8. The medicine delivery device as claimed in claim 1, wherein said transmission module further comprises a first locating block and a second locating block respectively mounted on opposing top and bottom ends of said transmission shaft to support said transmission shaft in said main housing for allowing said transmission shaft to be rotated in said first locating block and said second locating block by said transmission unit.

9. The medicine delivery device as claimed in claim 8, wherein said first locating block and said second locating block are hollow bearings.

10. The medicine delivery device as claimed in claim 1, wherein said transmission shaft is an internally threaded hollow shaft; said push rod is a screw rod threaded into the internally threaded said transmission shaft.

11. The medicine delivery device as claimed in claim 1, wherein said power supply unit is a rechargeable battery.

12. The medicine delivery device as claimed in claim 1, further comprising a connection unit mounted in a plug hole at a top side of said main housing and electrically coupled to said main control unit.

13. The medicine delivery device as claimed in claim 12, wherein said connection unit is a Micro USB.

14. The medicine delivery device as claimed in claim 1, wherein said main housing comprises a mounting groove located on an outer surface thereof, and a display unit mounted in said mounting groove and electrically coupled to said main control unit for displaying operating procedures or operating conditions.

15. The medicine delivery device as claimed in claim 14, wherein said display unit is a micro screen.

16. The medicine delivery device as claimed in claim 1, further comprising a buzzer disposed at one lateral side relative to said transmission unit and exposed outside said main housing and electrically coupled to said main control unit for generating sound.

17. The medicine delivery device as claimed in claim 14, wherein said main housing consists of a first shell and a second shell that are connected to each other, said first shell comprising a recessed groove located on an outer surface thereof below said display unit for the mounting of said push-button unit.

18. The medicine delivery device as claimed in claim 1, further comprising a syringe module mounted at a bottom side of said main housing for allowing said push rod of said transmission module to extend to the inside of said syringe module, said syringe module comprising:

a syringe barrel holding therein a liquid medicine;

a needle mounted in a bottom side of said syringe barrel; and a movable seal axially slidably mounted in said syringe barrel and movable by said push rod to expel said liquid medicine out of said syringe barrel through said needle.

19. The medicine delivery device as claimed in claim 18, wherein said movable seal is a piston.

20. The medicine delivery device as claimed in claim 18, wherein said syringe module further comprises a protective shell surrounding said syringe barrel, said protective shell consisting of two symmetrical shell halves and defining therein a shell chamber for accommodating said syringe barrel for allowing said needle to be exposed outside said protective shell.

* * * * *